United States Patent
Grabandt et al.

(10) Patent No.: US 10,100,463 B2
(45) Date of Patent: Oct. 16, 2018

(54) METHOD FOR NON-DESTRUCTIVE TESTING OF SYNTHETIC ROPES AND ROPE SUITABLE FOR USE THEREIN

(71) Applicant: TEIJIN ARAMID B.V., Arnhem (NL)

(72) Inventors: Otto Grabandt, Abcoude (NL); Bertil Van Berkel, Huissen (NL); Folkert Oosterhuis, Arnhem (NL); Tony Mathew, Wageningen (NL); Peter Gerard Akker, Doetinchem (NL)

(73) Assignee: TEIJIN ARAMID B.V., Arnhem (NL)

( * ) Notice: Subject to any disclaimer, the term of this patent is extended or adjusted under 35 U.S.C. 154(b) by 0 days.

(21) Appl. No.: 14/423,287

(22) PCT Filed: Sep. 3, 2013

(86) PCT No.: PCT/EP2013/068185
§ 371 (c)(1),
(2) Date: Feb. 23, 2015

(87) PCT Pub. No.: WO2014/037350
PCT Pub. Date: Mar. 13, 2014

(65) Prior Publication Data
US 2015/0225894 A1   Aug. 13, 2015

(30) Foreign Application Priority Data

Sep. 4, 2012 (EP) ................................. 12182921

(51) Int. Cl.
*D07B 1/14*   (2006.01)
*G01N 33/36*  (2006.01)
(Continued)

(52) U.S. Cl.
CPC ............. *D07B 1/145* (2013.01); *D07B 1/005* (2013.01); *G01N 21/3581* (2013.01); *G01N 21/95607* (2013.01); *G01N 23/02* (2013.01); *G01N 23/04* (2013.01); *G01N 27/9006* (2013.01); *G01N 33/365* (2013.01); *G01N 33/442* (2013.01); *D10B 2101/20* (2013.01); *D10B 2321/021* (2013.01); *D10B 2331/021* (2013.01); *D10B 2505/00* (2013.01); *G01N 2201/061* (2013.01); *Y10T 428/2913* (2015.01); *Y10T 428/2967* (2015.01)

(58) Field of Classification Search
CPC ....................................................... G01N 27/82
See application file for complete search history.

(56) References Cited

U.S. PATENT DOCUMENTS 4,197,695 A * 4/1980 Hughes ................ D07B 1/0673
156/433
5,834,942 A * 11/1998 De Angelis ............ D07B 1/025
187/226
(Continued)

FOREIGN PATENT DOCUMENTS

DE    20 2010 013519 U1    11/2010

OTHER PUBLICATIONS

Dec. 17, 2013 International Search Report issued in International Application No. PCT/EP2013/068185.
(Continued)

*Primary Examiner* — Noam Reisner
(74) *Attorney, Agent, or Firm* — Hamre, Schumann, Mueller & Larson, P.C.

(57) ABSTRACT

Methods for non-destructive testing of synthetic ropes is described, where the rope in use is subjected to X-ray, terahertz, permanent magnetic field or electromagnetic analysis to determine a pattern, the results of the analysis are compared with a standard pattern determined by the analysis, and the results of the comparison are used in determining whether the rope is fit for use; where the rope comprises at least two types of fibers, the first fiber type has a density which differs from the density of the second fiber type and the second fiber type is of the same polymer material as the first fiber type, but provided with a high-density or low-density material. Ropes suitable for use in this method are also described.

19 Claims, 1 Drawing Sheet

(51) Int. Cl.
*G01N 33/44* (2006.01)
*G01N 23/04* (2018.01)
*D07B 1/00* (2006.01)
*G01N 21/3581* (2014.01)
*G01N 21/956* (2006.01)
*G01N 23/02* (2006.01)
*G01N 27/90* (2006.01)

(56) References Cited

U.S. PATENT DOCUMENTS

| | | | |
|---|---|---|---|
| 6,289,742 B1 * | 9/2001 | De Angelis | B66B 7/06 |
| | | | 73/158 |
| 7,438,975 B2 | 10/2008 | Willemsen et al. | |
| 2003/0062225 A1 * | 4/2003 | Stucky | B66B 7/123 |
| | | | 187/393 |
| 2003/0062226 A1 | 4/2003 | Stucky et al. | |
| 2003/0089551 A1 * | 5/2003 | Kato | B66B 7/06 |
| | | | 182/1 |
| 2011/0259677 A1 | 10/2011 | Dudde et al. | |
| 2014/0266169 A1 * | 9/2014 | Huntley | G01D 1/00 |
| | | | 324/222 |

OTHER PUBLICATIONS

Dec. 17, 2013 Written Opinion cited in International Application No. PCT/EP2013/068185.

* cited by examiner

METHOD FOR NON-DESTRUCTIVE TESTING OF SYNTHETIC ROPES AND ROPE SUITABLE FOR USE THEREIN

BACKGROUND

During use, the properties of a rope decrease. In some applications, e.g., when the rope is used as mooring line, the rope suffers from tension-tension fatigue. That is, the rope is subjected to a cyclic increase and decrease of tension, and this has been found to detrimentally affect the properties of the rope. In other applications, e.g., where the rope is used over pulleys, the rope suffers from bending fatigue. That is, the properties of the rope deteriorate when the rope is subjected repeatedly to bending.

One of the key concerns of a rope user is to determine when a rope should be replaced. Replacing a rope entails substantial costs and effort, however. Not only the costs of the new rope need to be factored in, but also the costs associated with down-time of the unit wherein the rope is used, and the labour costs associated with the replacement. Therefore, it is undesirable to replace a rope too soon, that is, substantially before the end of its lifetime. On the other hand, the situation that a rope breaks or otherwise fails is unacceptable, and needs to be prevented.

Therefore, within the rope field methods have been developed to test the properties of the rope while it is in use, to allow the rope user to determine when the rope should be replaced. Testing the properties of a rope while it is in use is indicated in the field as non-destructive testing.

A first non-destructive testing method known in the art is magnetic field testing, wherein the object to be tested is brought into a magnetic field, and the presence of defects is detected through areas of flux leakage in the rope. A further method is eddy current testing wherein an alternating electrical current is passed through a coil producing a magnetic field. When the coil is placed near a conductive material, the changing magnetic field induces current flow in the material. These currents travel in closed loops and are known as eddy currents. Eddy currents produce their own magnetic field that can be measured and used to determine the presence of flaws in the rope.

While the methods specified above have shown their value in wire ropes, they are not directly applicable to synthetic ropes, as they rely on the magnetic and electrically conductive properties of the rope. Synthetic ropes are in principle very attractive to replace wire ropes in numerous applications, as they have a number of advantages, including lighter weight for the same strength, insensitivity to corrosion, and lower maintenance requirements. However, for synthetic ropes to be used in high risk applications, the availability of a method for testing the rope properties in use is required.

Methods for non-destructive testing of synthetic ropes are known. U.S. Pat. No. 6,886,666 describes the non-destructive testing of metallic and synthetic load bearing members. The load bearing member comprises a first, structural material (which can be a synthetic fiber) and at least one element of a second material which has a distinguishing characteristic from the first material.

The second material is used for detecting strain on the load bearing member.

The disadvantage of using a tracking fiber which is made from a different material is that the tracking fiber which is used to assess the condition of the load bearing member inherently possesses characteristics different from the first, structural material.

To overcome this disadvantage it would be advantageous to use a second material within the rope for assessing the condition of the rope which has more or less the same characteristics and properties (e.g. with regard to mechanical properties and behavior in the rope) as the first material.

The present invention provides such a method.

SUMMARY

The present invention pertains to a method for non-destructive testing of synthetic ropes wherein the rope in use is subjected to X-ray, terahertz, permanent magnetic field or electromagnetic analysis to determine a pattern, the results of the analysis are compared with a standard pattern determined by the analysis, and the results of the comparison are used in determining whether the rope is fit for use, wherein the rope comprises at least two types of fibers, wherein the first fiber type has a density which differs from the density of the second fiber type and wherein the second fiber type is of the same polymer material as the first fiber type, but provided with a high-density or low-density material.

The present invention also pertains to a rope suitable for use in the method of the present invention wherein the rope comprises at least two types of fibers, wherein the first fiber type has a density which differs from the density of the second fiber type and wherein the second fiber type is of the same polymer material as the first fiber type, but provided with a high-density or low-density material.

DETAILED DESCRIPTION OF THE EMBODIMENTS

In one embodiment, the standard pattern and the pattern of the rope in use are derived from a repeating oscillation pattern associated with the structure of the rope, and the comparison between the two patterns is a measure for the change in the repeating oscillation pattern associated with the structure of the rope caused by using the rope. This can be elucidated as follows. In essence there are two different types of ropes, namely parallel ropes, wherein the strands are arranged in parallel, and structured ropes, wherein the strands in the rope are combined through weaving, braiding, twisting, stranding, bunching, combinations thereof, and other methods known in the art. In these methods, the strands form regular oscillating patterns in the rope, with the exact pattern being dependent on the construction of the rope in question.

After manufacture, the oscillating patterns in the rope are regular over the rope length. During use, the oscillating patterns in the rope may change. They may, e.g., be lengthened by stretching of the rope, or they may become irregular due to the rope being used over pulleys or other apparatus. Therefore, the difference between the standard pattern derived from the repeating oscillation pattern associated with the structure of the rope and the pattern derived from the rope in use can serve as an indication for the changes in the rope, and therewith for the deterioration of the rope during use.

In another embodiment the pattern is not directly derived from the configuration of the second fiber type in the rope but it is derived from the signal output of the detection method (e.g. from image processing or spike analysis). This output can e.g. be a signal pattern, a spectrum or an image derived from the measured signal, a change in signal amplitude or frequency obtained from an X-ray, electromagnetic, permanent magnetic field or terahertz technique. This signal pattern can be compared with the signal pattern of a new rope. For example, a breakage of the second fiber type would interrupt the measured signal and therefore present another pattern than a new, not broken rope. The advantage of this embodiment is that the method of this invention can also be used for ropes comprising parallel strands, e.g. so-called UD ropes (unidirectional ropes).

In one embodiment the patterns are derived from X-ray transmission data. The use of X-ray transmission is advantageous, int. al., because it is well known for use in other applications, and therewith accessible technology. Further, patterns obtained through X-ray transmission can directly show the repeating oscillation pattern of the rope. Analysis of data generated through X-ray transmission relies on the detection of density differences. Therewith, the suitability of a rope for use in the method of the invention may be improved by increasing the density difference between the first and second fiber type in the rope.

In another embodiment the patterns are derived from terahertz analysis. Terahertz analysis uses terahertz electromagnetic radiation for non-destructive testing. With frequencies between 0.1 and 10 terahertz (THz), the spectral range of terahertz lies between microwaves and infrared radiation. The corresponding wavelengths range from 3 mm to 30 µm.

Terahertz waves unite the advantages of the two neighboring spectral regions: high penetration depth and low scattering combined with good spatial resolution are characteristic properties of terahertz waves. Unlike UV radiation or X-rays, for example, terahertz waves do not change the chemical structure. Consequently, they are not harmful to humans and present no health risks.

Terahertz analysis is based on the different amounts of absorption, scattering and reflection of terahertz radiation by different materials. Terahertz analysis can additionally be based on frequence-specific, spectroscopic behavior of different materials.

In another embodiment, a permanent magnetic field is used to determine a pattern of the rope. The permanent magnetic field is generated by the first fiber type which is comprised in the rope. An array of magnetic field detectors in close proximity to the rope can be used to derive the pattern. An example of such an array is a circular arrangement of detectors around the rope. Another example of such an array is a row of detectors along the length of the rope. Any combination of these arrangements is also possible.

In another embodiment electromagnetic analysis is used to determine the pattern. The electromagnetic analysis uses an electromagnetic field with a frequency in the range of 10 kHz to 5 GHz for non-destructive testing. The electromagnetic field is generated by a transmitter coil in close proximity to the rope, in some cases the rope can travel through the center of the coil. The electromagnetic field can also be generated between two plates of a capacitor between which the rope travels. Several configurations can be envisioned to extract status information from the rope using electromagnetic analysis.

The following embodiments are non-limiting examples of electromagnetic analysis. In one embodiment, the coil which transmits the electromagnetic field can be one of the components which determine the frequency of the electromagnetic field which is generated by the coil. In this case, the frequency of the electromagnetic field is influenced by the constitution of the rope.

In a second embodiment, a magnetic flux concentrator arrangement can be used. The transmitter coil is electrically driven by a high frequency carrier which is modulated in amplitude by a low frequency signal. The coil is placed perpendicular to the rope with a sensor between the rope and the coil which is sensitive to the electromagnetic field, e.g. a Hall sensor or a second, receiver coil. Depending on the proximity of rope components which influence the electromagnetic field to the sensor, the field will become stronger or weaker. The signal from the receiver coil can be converted using synchronous detection by which only the low frequency signal remains. In this case, the amplitude of the low frequency signal contains the information about the constitution of the rope.

In another embodiment, the rope travels through the transmitter and receiving coils. The receiving coils are located on both sides of the transmitter coil. Signals from both receiving coils can be used separately and as a difference signal to obtain the information about the constitution of the rope.

In another embodiment, the rope travels between two plates of a capacitor. In case the capacitor is one of the frequency determining components, the proximity of rope components which influence the electromagnetic field will have effect on the generated frequency. The frequency of the electromagnetic field will contain information about the constitution of the rope.

The electromagnetic and permanent magnetic analyses used in the invention are different from the magnetic flux leakage method widely used for testing of steel wire ropes.

Depending on the nature of the rope, it may be desirable to adapt the composition of the rope to make it particularly suitable for the one of the methods used in the present invention.

Analysis of data generated through X-ray, terahertz, permanent magnetic field or electromagnetic transmission relies on the detection of differences between the first fiber type and the second fiber type. For X-ray, this is a difference in density, while for terahertz it is the different absorption, scattering or reflection spectrum, for permanent magnetic analysis it is the permanent magnetic permeability and for electromagnetic analysis they are the magnetic permeability and dielectric properties, depending on the specific detection technique chosen. Therewith, the suitability of a rope for use in the method of the invention may be improved by increasing the differences with regard to the measured characteristic in the rope. Many materials which have a higher or lower density than the second fiber type also possess different properties with regard to terahertz absorption, reflection or scattering, electromagnetic and permanent magnetic properties. To effect this, the rope comprises at least two types of fibers, wherein the first fiber type has a density which differs from the density of the second fiber type.

In the present specification, the term rope will be used for the final product. The term fiber is used for the smallest individual element in the rope, e.g. the polymer fiber or tape. The term cord is used for a longitudinal association of fibers, associated together by, e.g., twisting. The term strand is used for one or more cords which, together with other strands, are combined to form a structured rope.

Within the context of the present specification the term fiber refers to longitudinal elements the largest dimension of which, the length, is larger than the second smallest dimension, the width, and the smallest dimension, the thickness. More in particular, the ratio between the length and the width generally is at least 10. The maximum ratio is not critical to the present invention and will depend on processing parameters. Accordingly, the fibers used in the present invention encompass monofilaments, fibers comprised of multiple filaments (so-called multifilament fibers) but also tapes, strips, and other longitudinal elements having a regular or irregular cross-section.

There are various ways to manufacture ropes comprising at least two types of fibers, with the first fiber type having a density which differs from the density of the second fiber type.

In one embodiment, the first fiber type is present in an amount of at least 60 wt. % of the rope, and contributes to the rope properties, and the second fiber type is present in an amount of at most 40 wt. % of the rope and contributes to the possibilities for the pattern determination by X-ray, terahertz, permanent magnetic field or electromagnetic analysis. In this embodiment, the second fiber type may be regarded as a "tracking fiber".

It should be noted that the indication for the second fiber type that it contributes to the possibilities for X-ray, terahertz, permanent magnetic field or electromagnetic pattern determination does not mean that it cannot or should not contribute to the rope properties also.

It may be preferred for the rope to comprise the first fiber type in an amount of at least 70 wt. %, in particular at least 80 wt. %. As a maximum, an amount of 99.99 wt. % may be mentioned in general. The second fiber type may in some embodiments be present in an amount of at most 30 wt. %, in particular at most 20 wt. %. As a minimum value, an amount of at least 0.01 wt. % may be mentioned in general. Determination of the amount of tracking fiber suitable for a particular situation depends upon a number of parameters. A first parameter is the amount of fiber required to ensure that the distribution of the second fiber type throughout the rope is such that changes in the pattern derived from X-ray, terahertz or electromagnetic analysis originating from the second fiber type are representative for changes in properties of the rope. A larger number of strands may require a larger amount of fiber, to ensure that the fiber can be incorporated in a sufficient number of strands to obtain a suitable pattern. A relatively small density difference between the first fiber type and the second fiber type may also require a larger amount of second fiber type to ensure that a suitable pattern is obtained.

Accordingly, the amount of tracking fiber in the rope is dependent on the rope diameter, type of high density or low-density material and the amount of such material on the fiber. The higher the density of the material, the better is the visibility in e.g. X-ray technique. The visibility can also be adjusted by using one tracking fiber per rope, multiple tracking fibers in a strand of the rope, a full strand of tracking fibers or even tracking fibers inserted in several strands of the rope.

The tracking fiber may be incorporated into the rope in various manners. In one embodiment it is included in a strand together with fibers of the first fiber type. In another embodiment it is used as a separate strand. The rope can include one or more of such strands.

The rope can e.g. be obtained by braiding, twisting, beading of strands, stranding, spiraling, unidirectional laying of parallel strands or any combination thereof. For example, twisted and parallel laid fibers or strands can be combined in one rope.

The density of the second fiber type may be higher or lower than the density of the first fiber type. In one embodiment, the density of the second fiber type is higher than that of the first fiber type. The second fiber type is obtained by providing the first fiber type with a low-density or high density material.

Low density material means that the material has a lower density than the first fiber material. High density material means that the material has a higher density than the first fiber type.

If for example the first fiber type is aramid, the density of high density material is higher than 1.4 g/cm$^3$, preferably, the high density material has a density higher than 2 g/cm$^3$.

If the first fiber type itself has a lower density, as e.g. polyethylene tape which has a density of ca. 0.8 g/cm$^3$, the high density material provided onto the first fiber type can have a lower density as long as it is higher than the density of the first fiber type. However, for better detection it is preferred that the high density material has a density of at least 1.5 g/cm$^3$, preferably of at least 1.8 g/cm$^3$, more preferably of at least 2 g/cm$^3$ and even more preferably of at least 3 or 4 g/cm$^3$.

This embodiment is presently considered preferred, because it is believed to result in improved detectability of the second fiber. The density of the low-density or high-density material refers to the density of the material which is provided to the first fiber type, not the density of the second fiber including the fiber.

In one embodiment a low-density material is provided to the first fiber type to obtain the second fiber type. This can be especially advantageous for terahertz detection.

The second fiber type is of the same polymer material as the first fiber type, but provided with a high-density or low-density material. When the second fiber type is of the same polymer material as the first fiber type, it is believed that the behavior of the second fiber type is closely related to the behavior of the first fiber type. This is believed to result in a good match between the pattern derived from X-ray, terahertz, permanent magnetic field or electromagnetic analysis on the second fiber type of the rope in use and the damage suffered by the first fiber type of the rope in use.

The high-density or low-density material may be provided to the second fiber type of the same polymer material as the first fiber type in various manners. In one embodiment, the high-density or low-density material is adhered to the first fiber type using e.g. glue or in a coating process. In one embodiment, fibers, cords, or strands are coated with a high-density or low-density material. As a high-density material metals and/or derivates or alloys thereof can be applied. Examples of suitable metals are alkali metals, alkaline earth metals, transition metals, lanthanoids and actinoids, such as cerium, copper, nickel, cerium, rubidium, zinc, iron, zirconium, tantalum, barium, silver, gold, platinum, titanium or irridium. Derivatives of such metals include salts (as e.g. nitrides, carbides, sulphates), soaps, oxides and organo-metal complexes.

In one embodiment the metal, metal oxide or a metal salt can be applied. Suitable metals, metal oxides and metal salts are e.g. pure zirconium dioxide, stabilized zirconium dioxide, zirconium nitride, zirconium carbide, tantalum pentoxide, barium sulphate, silver iodide, ferric oxides or zinc oxide.

Zinc oxide (ZnO) is a suitable high-density material, it has a density of ca. 5.6 g/cm$^3$ which is significantly higher than the density of aramid fiber or PE tape.

However, also non-metal materials as e.g. halogens with a higher density than the first fiber type can be employed as high density material. This includes also derivatives, as salts, oxides, soaps and organo-halogen complexes. For example, iodine or bromine derivates, as e.g. alkali iodides, iodated aromatics, iodated aliphatics, iodated oligomers, iodated polymers as well as mixtures and alloys of such substances.

Any combination of different high-density materials can also be applied.

Low-density materials which can be applied to the first fiber type can e.g. be caffeine or aspirine.

In one embodiment more than one high-density or low-density material is applied to the first fiber type. This means that the second fiber type comprises the first fiber type and more than one low-density or high-density material. The advantage of this embodiment is that the same second fiber type can be used in different analysis techniques. In another embodiment a rope comprises more than one second fiber type, each of the second fiber types provided with a different low-density or high-density material. Also in this embodiment the same rope can be subjected to different analysis techniques.

In another embodiment the high-density or low-density material is chosen such that it can be detected with different analysis techniques. For example, if a metal or metal derivate is provided to the first fiber type, this metal or metal derivate can be detected with X-ray analysis because of the difference in density but also with terahertz analysis, because of the difference in absorption, scattering or reflection between the first fiber type and the metal or metal derivate. If such a metal or metal derivate is ferromagnetic or paramagnetic it can also be detected via electromagnetic analysis as described above or by using a permanent magnetic field.

Magnetism is a class of physical phenomena that includes forces exerted by magnets on other magnets. It has its origin in electric currents and the fundamental magnetic moments of elementary particles. These give rise to a magnetic field that acts on other currents and moments. All materials are influenced to some extent by a magnetic field. The strongest effect is on permanent magnets, which have persistent magnetic moments caused by ferromagnetism. Most materials do not have permanent moments. Some are attracted to a magnetic field (paramagnetism); others are repulsed by a magnetic field (diamagnetism); others have a much more complex relationship with an applied magnetic field (antiferromagnetism or ferrimagnetism).

The embodiment where second fiber types comprising different high or low density materials are present in a rope or a pattern derived from one high or low density material can be obtained with different techniques is especially advantageous. In such a case a rope comprising the first and second fiber type can be subjected to different analysis methods described in this invention. For example, electromagnetic analysis can be used for quick testing while X-ray analysis can be used for more detailed inspection of the rope. It is advantageous to use a method which can be used at higher testing speeds continuously and online first. This inspection can take place during use of the rope. A slower inspection method can then be used for in-depth detailed inspection.

The material of different density can be applied in different forms, also depending on the application technique, e.g. solutions with organic solvent or as aqueous solution, dispersed as powder in (curable) resins or hotmelts. In one embodiment a dispersion of the high-density or low-density material in a medium such as wax or resin is made and combined with a wax or resin of a second emulsion. The emulsion and dispersion can subsequently be combined to result in a composition with different concentrations of the high- or low-density material which is subsequently applied to the first fiber type to result in the second fiber type.

To apply the material of high or low density or a composition comprising said material to the fibers, every method is suitable by means of which the desired amount of material solids can be applied to the fibers.

The material of different density can be applied to the first fiber type by a number of techniques not limited to glueing, coating, application as a finish, spraying or lamination, which is especially advantageous for tapes.

For example, the material or composition can be applied during the production process of the fibers, using a nozzle or with an applicator or with a kiss roll, after the washing and prior to the drying, after which the fibers are dried and wound up. The application with a kiss roll means that a rotating roll is partially immersed in a bath, in which the material of higher or lower density is present, e.g. as an aqueous solution. A film forms on the part of the roll protruding from the bath. The fibers are brought into contact with the film and thereby finished.

Further, the material or composition application can also be implemented in a process downstream from the fiber production. For this purpose, the fibers can be e.g. unwound from the roll and brought into contact with the material or composition. It is also possible to implement the application in two or more steps that take place in series, wherein e.g. a first step occurs during the production process of the fibers after the washing and prior to the drying, and a second step occurs in a process downstream of the fiber production.

The rope suitable for use in the method according to the invention contains synthetic fibers. The high-strength polymer fibers known in the art are suitable for use in the rope and the method of present invention, as e.g. polyamide, polyarylates, polyester, carbon fibers, polyacrylonitril (PAN, including stabilized PAN), polybenzazole (including polybenzoxazole and polybenzothiazole homo- and copolymers) polypropylene, aramid and PE fibers. Ropes can also be made from a combination of such fibers, giving hybrid ropes comprising different types of synthetic polymers.

In one embodiment, aramid fibers are used, i.e. para-aramid or meta-aramid fibers, preferably para-aramid fibers. Meta-aramid is shorthand for meta-linked aromatic polyamides, such as poly (m-phenylene isophthalamide). Para-aramid is shorthand for para-oriented aromatic polyamides which are condensation polymers of a para-oriented aromatic diamine and a para-oriented aromatic dicarboxylic acid halide. As typical para-aramids are mentioned the aramids which structures have a poly-para-oriented form or a form close thereto, such as poly(paraphenylene terephthalamide), poly(4,4'-benzanilide terephthalamide), poly(para-phenylene-4,4'-biphenylenedicarboxylic acid amide) and poly (paraphenylene-2,6-naphthalenedicarboxylic acid amide or copoly(para-phenylene/3,4'-oxydiphenylene terephthalamide). The use of poly(paraphenylene terephthalamide), also indicated as PPTA may be preferred. Para-aramid fibers are commercially available under, in al., the trade names Twaron® and Technora®, meta-aramid fibers are commercially available under, in al., the trade name Teijinconex®.

In another embodiment of the method or the rope as first fiber type polyethylene is used. Polyethylene according to this invention includes homopolymers of ethylene and copolymers of ethylene with a co-monomer which is another alpha-olefin or a cyclic olefin both with generally between 3 and 20 carbon atoms. Examples include propene, 1-butene, 1-pentene, 1-hexene, 1-heptene, 1-octane, cyclohexene etc. The use of dienes with up to 20 carbon atoms is also possible, e.g. butadiene, 1-4 hexadiene or dicyclopentadiene. The amount of (non-ethylene) alpha-olefin in the ethylene homopolymer or copolymer used in the process according to the invention preferably is at most 10 mole %, preferably at most 5 mole %, more preferably at most 1 mole %. If a (non-ethylene) alpha-olefin is used, it is generally present in an amount of at least 0.001 mol %, in particular at least 0.01 mole %, still more in particular at least 0.1 mole %. Obviously, this means that where ethylene is mentioned as a monomer that the monomer can also include at most 10 mole %, preferably at most 5 mole %, more preferably at most 1 mole % of a (non-ethylene) alpha-olefin monomer or cyclic olefin monomer based on the total amount of monomers.

Preferably, ultra high molecular weight polyethylene (UHMWPE) is used. UHMWPE means that the average molecular weight of the polyethylene is higher than 0.5 million g/mol.

It is well-known how by solid-state processing tapes can be produced from polyethylene. For example, EP2385963 describes how a film and tapes can be produced from polyethylene. Such tapes can further processed to obtain fibers or fibrillated tapes, as e.g. described in EP2300644. The polyethylene tapes or fibers can be used in the method and rope according to the invention as first fiber type and after having been provided with a material of different density as second fiber type.

Depending on the synthetic fiber used in the rope the analysis method can be adapted to obtain optimal results. For example, when using terahertz radiation it is advantageous to use terahertz radiation of a wavelength or frequency which is not reflected, scattered or absorbed by the synthetic fiber of the rope, i.e. by the first fiber type, but which is reflected, absorbed or scattered by the second fiber type. For aramid this means that radiation of 0.1-1 THz is best suited, while for polyethylene 0.1-10 THz is optimal.

The embodiments of the first and second fiber types described for the method of the present invention which have been described above are also applicable to the first and second fiber type comprised in the rope of present invention.

In one embodiment the rope according to the present invention comprises a high density material which comprises a metal, and/or a derivative or alloy thereof, preferably copper, nickel, cerium, rubidium, zinc, iron, zirconium, tantalum, barium, silver, gold, platinum, titanium, copper, nickel or iridium, more preferably zinc.

In another embodiment the rope according to the invention comprises the first and the second fiber type, where the first fiber type is present in an amount of at least 60 wt. % of the rope, and contributes to the rope properties, and wherein the second fiber type is present in an amount of at most 40 wt. % of the rope and contributes to the possibilities for pattern determination.

In another embodiment in a rope according to the invention the distribution of the second fiber type throughout the rope is such that changes in the X-ray, terahertz, permanent magnetic field or electromagnetic pattern originating from the second fiber type are representative for changes in properties of the rope.

If so desired, the rope according to the invention or strands used therein may be surrounded by a mantle, jacket, sleeve, wrap, tape bonding, or polymer cover, e.g., to protect the rope from environmental conditions or to provide mechanical protection to the rope.

The method and rope according to the invention may be used in numerous applications. They are particularly suitable for applications where ropes suffer from tension-tension fatigue and bending fatigue, e.g., in mining operations or off-shore oil and gas operations, e.g., as mooring lines, tow lines, winch lines, and in lifting and installation applications.

BRIEF DESCRIPTION OF THE DRAWINGS

The following examples and figures describe the invention in more detail but do not limit the scope of the invention.

EXAMPLE 1—X-RAY INSPECTION OF ARAMID FIBER BUNDLES

Tracking fibers, i.e. second fiber type with a coating of high density materials were prepared for X-ray inspection. The tracking fiber in this case is an aramid fiber coated with a high density material. A coating composition was prepared from a first emulsion comprising wax and a second dispersion of ZnO. The first emulsion was an emulsion available from BYK CERA containing 35 wt % of wax (commercially available as Aquacer 1547). The second dispersion was a dispersion available from Evonik containing 34 wt % of ZnO (commercially available as PI VP Disp ZnO 20 DW). The first emulsion and the second dispersion were mixed together to have different concentrations (8, 16 and 24 wt % based on the weight of the composition) of the high density material ZnO in the composition. The composition was brought to a total solid content of 32 wt %.

The above described composition was applied to Twaron 1000 (1680 dtex/f1000) fibers using a liquid applicator. The composition was applied onto the fibers in an amount of 12 wt % (based on the weight of the fiber), corresponding to a ZnO concentration of 3, 6 and 9 wt % (based on the weight of the fiber respectively. Immediately after application of the composition, the fiber was dried in an oven at 160° C. for a time of about 10 sec.

Figure 1:
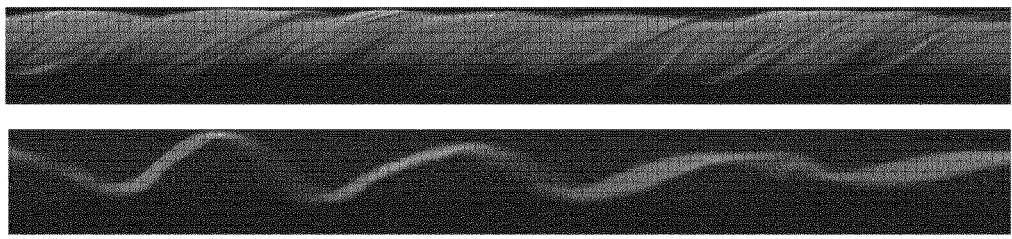
FIG. 1 shows an optical (upper panel) and XRF image (lower panel) of a twisted bundle of aramid fibers comprising a fiber coated with a ZnO-comprising composition.

This "tracking fiber" was then tested for its visibility in an X-ray technique. Towards this end, one tracking fiber was bundled together with 20 untreated aramid fibers of the same type. This bundle was twisted to obtain a periodic structure within the bundle giving an oscillatory pattern in the rope construction. The fiber bundle was loaded onto a sample holder in a X-ray fluorescence machine (XRF). XRF is widely used for elemental analysis and chemical analysis particularly in the detection of metals. A scanning of the fiber bundle over a particular area gives images of the bundle and the position of the tracking fiber. Such an image using a tracking fiber containing ZnO is shown in FIG. 1 in the lower panel (shown is the sample with 9 wt % ZnO on fiber). In the upper panel an optical image of the same fiber bundle is shown.

EXAMPLE 2—X-RAY DIFFERENTIAL PHASE CONTRAST IMAGING OF ARAMID ROPE

Figure 2:
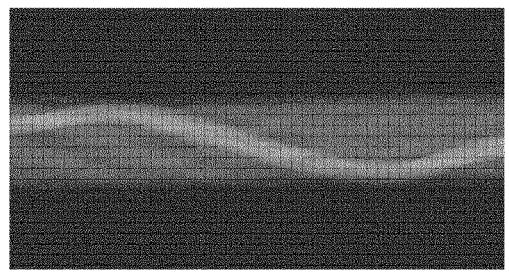
FIG. 2 shows an X-ray differential phase contrast image (absorption) of a rope comprising bundles of aramid fibers and a bundle of aramid fibers coated with a composition comprising ZnO

The ZnO-comprising tracking fiber from example 1 was used to produce an aramid rope of 10 mm diameter. The rope consists of 12 twisted strands and each strand contains 32 fibers. One strand of 32 fibers consists only of tracking fibers. The rope sample was then scanned using an X-ray differential phase contrast imaging (XPCI) technique. The parameters used for the measurement are: X-ray tube voltage=40 kV; X-ray tube current=22.5 mA; Pixel size: 45 micrometers; exposure time: 1.5 min per image; distance between source and detector=~1.4 m. An image of the rope samples containing ZnO tracking fiber from XPCI in absorption mode is given in FIG. 2 (shown is the sample with 9 wt % ZnO on yarn).

As is clear from the images, the pattern of the tracking fiber is well visible. This also means that information on deviations in the spatial phase between the strands can also be obtained from these images. These informations can be used to assess the condition (e.g. breaks, elongation) of the rope.

The coated tracking fiber and the non-coated fiber were tested for their mechanical properties. Both samples were tested on a standard tensile tester according to ASTM-D7269-07 ("Standard Test Methods for Tensile Testing of Aramid Yarns") under the following conditions: scan frequency—50 Hz, pre-tension 20 mN/tex, clamp speed—250 mm/min, gauge length—500 mm.

The results are shown in table 1. The results show that the properties of the first fiber type, in this case Twaron 1000 and the tracking fiber, in this case Twaron 1000 with ZnO differ only little. Therefore, the mechanical properties are similar and the tracking fiber (second fiber type) is expected to be a good indicator for the condition of the first fiber type.

TABLE 1

Comparison of the mechanical properties of the first fiber type (uncoated, Twaron1000) and second fiber type (coated with a high density material, ZnO tracking fiber)

| Mechanical characteristic | Twaron1000 | ZnO-coated tracking fiber, based on Twaron1000 |
|---|---|---|
| Breaking force [N] | 375 | 381 |
| Breaking tenacity [mN/tex] | 2187 | 1988 |
| Modulus [GPa] | 53 | 45 |
| Elongation at break [%] | 3.5 | 3.7 |
| Toughness at rupture [J/g] | 36 | 34 |

EXAMPLE 3—X-RAY INSPECTION OF UHMWPE ROPES

In a similar way as described in examples 1 and 2 compositions containing high density materials were applied to UHMWPE samples. For this purpose, UHMWPE (ultra-high molecular weight polyethylene) tapes (Endumax®, from Teijin Aramid) were used. Experiments were carried out with regular 2 mm wide tapes and also on fibrillated polyethylene (PE) tapes.

A composition was prepared from a first emulsion comprising a medium of styrene isoprene block copolymer and a second dispersion of ZnO. The first emulsion was an emulsion available from Trüb Emulsions containing 36 wt % of solids (commercially available as Tecpol KW 2401/20). The second dispersion was a dispersion available from Evonik containing 34% of ZnO (commercially available as PI VP Disp 20 DW). The first emulsion and the second dispersion were mixed together to have different concentration (8, 16 and 24 wt % based on the weight of the composition) of ZnO in the composition. The composition was brought to a total solid content of 32 wt %.

Figure 3:
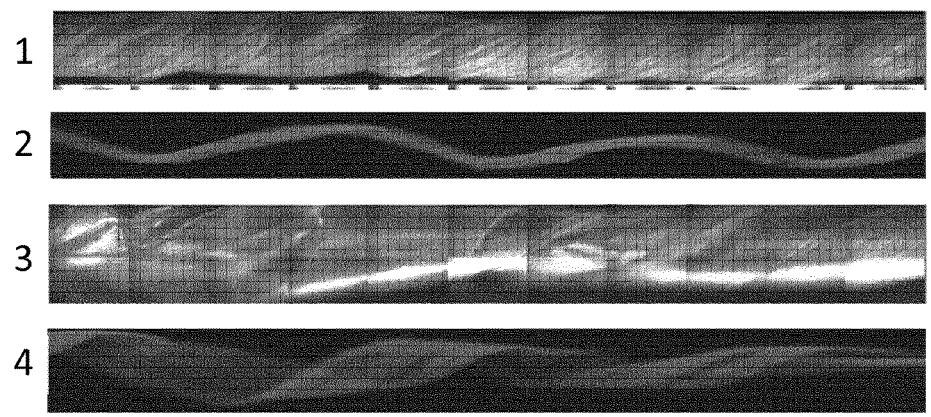
FIG. 3 shows optical (panels 1 and 3) and XRF images (panels 2 and 4) of UHMWPE tape bundles comprising a UHMWPE tape coated with a ZnO-comprising composition. Panels 1 and 2 show tapes which were fibrillated, while panels 2 and 4 show 2 mm wide tapes.

In a similar way as for the fibers, the composition was applied to the UHMWPE tapes and fibrillated tapes. For the XRF measurements, as mentioned in the case of aramid fibers, one tracking tape was bundled together with 20 uncoated PE tapes. This was done for tapes and fibrillated tapes separately. The bundle was then given a twist in order to obtain an oscillatory pattern of the tracking fiber within the bundle. The bundles were tested using XRF imaging. FIG. 3 shows images of the UHMWPE bundles containing one tracking fiber/tape (shown is the sample with 24 wt % ZnO coating composition). In the first and third panel an optical image of the bundles is shown and in the second and fourth panel an XRF image of the bundles is shown. Panel one and two show the results for fibrillated tapes (multiple images compiled) and panels three and four show results for tapes (multiple images compiled). The images show that the tracking fiber can be distinguished from the non-coated fibers and gives a well-visible image in the XRF imaging. A break or other disturbance of the tracking fiber could be identified in this way.

The invention claimed is:

1. A method for non-destructive testing of a synthetic rope, comprising:
    subjecting a synthetic rope during use to an X-ray analysis;
    receiving a pattern of the synthetic rope from the X-ray analysis;
    comparing the pattern to a standard pattern determined by the analysis; and
    determining, based on the comparison, a condition of the synthetic rope;
    wherein the synthetic rope comprises a first fiber type and a second fiber type,
        the first fiber type has a density that is different from a density of the second fiber type,
        the second fiber type and the first fiber type are formed of a same polymer material, and
        the second fiber type comprises a further material having a density higher than a density of the polymer material, wherein the further material is adhered to the second fiber type.

2. The method according to claim 1, wherein the further material is adhered to the second fiber type by a glue or a coating process.

3. The method according to claim 1, wherein the further material comprises a metal.

4. The method according to claim 3, wherein the metal is at least one metal selected from a group consisting of copper and nickel.

5. The method according to claim 1, wherein
    the standard pattern and the pattern of the synthetic rope are derived from a repeating oscillation pattern associated with a structure of the synthetic rope, and
    the pattern of the synthetic rope is compared to the standard pattern for a change in the repeating oscillation pattern associated with the structure of the synthetic rope caused by use.

6. The method according to claim 1, wherein
    the first fiber type is present in an amount of at least 60 wt. % of the synthetic rope, and contributes to properties of the synthetic rope during use, and
    the second fiber type is present in an amount of at most 40 wt. % of the synthetic rope and contributes to possibilities for pattern determination during use.

7. The method according to claim 1, wherein distribution of the second fiber type throughout the synthetic rope is such that changes in the pattern derived from the X-ray analysis originating from the second fiber type are representative for changes in properties of the synthetic rope during use.

8. The method according to claim 1, wherein the first fiber type and the second fiber type are made from aramid.

9. The method according to claim 1, wherein the first fiber type and the second fiber type are made from the polymer selected from a group consisting of para-aramid.

10. A synthetic rope suitable for non-destructive testing, comprising:
   a first fiber type and a second fiber type, wherein the first fiber type and the second fiber type are made of a same polymer material;
   a density of the first fiber type is different from a density of the second fiber type; and
   the second fiber type comprises a high density further material, wherein the high density further material is adhered to the second fiber type, and the high density further material has a density higher than a density of the polymer material.

11. The synthetic rope according to claim 10, wherein the high density material is adhered to the second fiber type using glue or a coating process.

12. The synthetic rope according to claim 10, wherein the high density material comprises a metal.

13. The synthetic rope according to claim 12, wherein the at least one material is selected from a group consisting of copper and nickel.

14. The synthetic rope according to claim 10, wherein the first fiber type is present in an amount of at least 60 wt. % of the rope, and contributes to the rope properties, and
   the second fiber type is present in an amount of at most 40 wt. % of the rope and contributes to possibilities for pattern determination.

15. The synthetic rope according to claim 10, wherein a distribution of the second fiber type throughout the rope is such that changes in an X-ray analysis originating from the second fiber type are representative for changes in properties of the rope.

16. The synthetic rope according to claim 10, wherein the first fiber type is aramid.

17. A method comprising:
   carrying out an application in which a rope suffers from tension-tension fatigue or bending fatigue,
   wherein the rope is a synthetic rope of claim 10.

18. The method of claim 17, further comprising:
   obtaining a pattern by subjecting the synthetic rope that has been used in the application to an X-ray analysis;
   comparing the pattern to a standard pattern determined by the analysis; and
   determining, based on the comparison, a condition of the used synthetic rope.

19. The synthetic rope according to claim 10, wherein the first fiber type and the second fiber type are made from a polymer selected from a group consisting of para-aramid.

* * * * *